(12) United States Patent
Hartmer

(10) Patent No.: US 8,604,426 B2
(45) Date of Patent: Dec. 10, 2013

(54) RADICAL IONS FOR ELECTRON TRANSFER DISSOCIATION

(71) Applicant: Bruker Daltonik GmbH, Bremen (DE)

(72) Inventor: Ralf Hartmer, Hamburg (DE)

(73) Assignee: Bruker Daltonik GmbH, Bremen (DE)

( * ) Notice: Subject to any disclaimer, the term of this patent is extended or adjusted under 35 U.S.C. 154(b) by 0 days.

(21) Appl. No.: 13/772,701

(22) Filed: Feb. 21, 2013

(65) Prior Publication Data

US 2013/0164174 A1  Jun. 27, 2013

Related U.S. Application Data

(62) Division of application No. 12/617,367, filed on Nov. 12, 2009, now Pat. No. 8,461,522.

(51) Int. Cl.
| | |
|---|---|
| *H01J 49/10* | (2006.01) |
| *G01N 33/68* | (2006.01) |
| *B01D 59/44* | (2006.01) |

(52) U.S. Cl.
USPC ..... 250/288; 250/281; 250/423 R; 250/493.1; 422/63

(58) Field of Classification Search
USPC ............. 250/288, 281, 423 R, 493.1; 422/63
See application file for complete search history.

(56) References Cited

U.S. PATENT DOCUMENTS

| | | | |
|---|---|---|---|
| 7,456,397 B2 * | 11/2008 | Hartmer et al. ............... | 250/292 |
| 8,198,583 B2 * | 6/2012 | Brekenfeld et al. .......... | 250/282 |
| 8,461,522 B2 * | 6/2013 | Hartmer ........................ | 250/288 |
| 2013/0115711 A1 * | 5/2013 | Hartmer ........................ | 436/173 |

* cited by examiner

*Primary Examiner* — Nikita Wells
(74) *Attorney, Agent, or Firm* — Robic, LLP

(57) ABSTRACT

Radical anions for use in the fragmentation of positively charged biopolymer ions by means of electron transfer are produced from substances previously unknown for use as ETD production substances. The inventive substances produce radical anions that lead to electron transfer dissociations with a high yield of fragment ions. The substances have high volatility that allows them to be kept in unheated containers outside the vacuum system and transported into the vacuum system to an in vacuum electron attachment ion source via unheated lines and low molecular weights that allow the measurement of even very light fragment ions. In one embodiment, a suitable substance is 1-3-5-7-cyclooctatetraene.

9 Claims, 2 Drawing Sheets

RADICAL IONS FOR ELECTRON TRANSFER DISSOCIATION

BACKGROUND

The invention relates to the fragmentation of biopolymer ions with multiple positive charges by means of electron transfer (ETD=electron transfer dissociation) in reactions with radical anions. The sequences of the basic building blocks of biopolymers and their posttranslational modifications (PTM) are nowadays predominantly determined using tandem mass spectrometers. A key technology used for this is fragmentation of the biopolymer ions. There are two fundamentally different types of fragmentation—ergodic and non-ergodic or electron-induced—and a number of methods are known for both of these.

Peptides and proteins in particular will be considered below as biopolymers. Electron-induced fragmentation of peptide or protein ions is complementary to ergodic fragmentation, first of all because it cleaves the chain of amino acids at different amino acid locations, and secondly because it does not cut off the side chains of the posttranslational modifications during fragmentation, as is done by ergodic fragmentation. Comparing the fragment ion spectra obtained from ergodic and non-ergodic, electron-induced fragmentations allows both the sequences and the modifications to be read.

The simplest electron-induced method is electron transfer dissociation (ETD), which occurs as a reaction between multiply positively charged analyte ions and special radical anions. By using particular species of negative reactant ions in order to cleave biopolymer ions with multiple positive charges, particularly peptide or protein ions, an electron is transferred to the analyte ion which immediately experiences a fracture of the backbone chain. The reactant ions are usually radical anions of the form $M.^-$, which readily donate electrons. The prior art is described in patents US 2005/0199804 A1 (D. F. Hunt et al.) and DE 10 2005 004 324 B4 (R. Hartmer and A. Brekenfeld). Both these documents describe the fragmentation of peptide or protein ions with multiple positive charges by reactant anions using this method.

For the electron transfer dissociation method, knowledge of substances for the generation of suitable radical reactant ions is crucial. These substances must be capable of quickly and very efficiently binding electrons stably, but only weakly, in special electron attachment ion sources. Favorable ETD substances so far known have low but still positive electron affinities in the region of approximately $0.55\pm0.25$ eV. The electrons are thus weakly bound to these substances and can easily be removed by positively charged ions and transferred to them.

The fundamental relationships between electron affinity and electron transfer are presented in the comprehensive review article by P. Kebarle and S. Chowdhury, Chem. Rev. 1987, 7, 513-534, "Electron Affinities and Electron-Transfer Reactions".

The patent of D. F. Hunt et al. cited above explains that such substances are found in the group of polycyclic aromatic hydrocarbons. Specifically, the substances anthracene, naphthalene, fluorene, phenanthrene, pyrene, fluoranthene, chrysene, triphenylene, perylene, 2,2'-biquinoline, acridine and others are listed. As far as recorded in the NIST database (NIST chemistry webbook), these substances have electron affinities (EA) between 0.3 and 0.8 electronvolts. Fluoranthene (EA=6.7 eV) and 2,2'-biquinoline are emphasized as being particularly suitable for pure electron transfer dissociation with a high yield of fragment ions and without a significant proportion of proton transfer reactions. With the other substances (except for perylene), as can be seen in Table 1 of the cited patent, the electron attachment ion source also supplies non-radical anions of the form $(M-1)^-$, which result in undesirable proton transfer reactions. Therefore, these polycyclic aromatics are not all equally useful for ETD.

A high effectiveness of the anions of a substance for ETD means that, on the one hand, a high yield of fragment ions of more than 50% of the ions to be dissociated is obtained and, on the other hand, the proportion of protein transfer reactions is less than 30%, preferably less than 10%. In this sense, fluoranthene and 2,2'-biquinoline are particularly effective for ETD.

However, these polycyclic aromatics, including fluoranthene, which has until now been known as very effective for ETD, have a very low vapor pressure in the order of 1 pascal at 20° Celsius, or even well below that. In electron attachment ion sources, the substances must be present with partial pressures of approximately 100 to 1000 pascal; the polycyclic aromatics therefore have to be heated in their container to between 50° and 250° C., and fed through heated lines to a heated electron attachment source. This makes the equipment difficult to design if the substance container is to be installed outside the vacuum system. The difficulties particularly concern feeding the heated gas line through the unheated wall of the vacuum system without generating a cool location where the substance vapor will condense.

In the prior art, therefore, a much simpler solution is usually applied. This involves mounting the heated substance container in the vacuum system close to the electron attachment source, or even heating the substance container by means of the electron attachment ion source, which is itself automatically heated sufficiently by the thermionic cathode required for electron emission. The disadvantage of this arrangement, however, is that in order to refill the container, not only must the container and the electron attachment source be cooled, but also the vacuum system must be vented and opened. Venting the vacuum system is, however, to be avoided whenever possible in mass spectrometry, as a considerable amount of time and effort are needed to restart the mass spectrometer, and recalibrating the mass scale and other settings are usually necessary. A further disadvantage is that it is difficult to design the equipment in such a way that the supply of substance to the electron attachment source can be interrupted during pauses in measurement or during measurements that do not use ETD. Consequently, in most cases, no method of interruption is provided; but this means continuous consumption of the ETD substances and therefore more frequent refilling.

In addition to electron transfer dissociation, other kinds of reaction between analyte ions with multiple positive charges and particular species of negatively charged ions can reduce the number of the charges on each of the positive analyte ions ("PTR"=proton transfer reactions, also known as "charge stripping"). This requires different kinds of anion, usually non-radical anions. In favorable cases these can be obtained from the same substances in special, switchable electron attachment ion sources (patent application DE 10 2006 049 241 A1; R. Hartmer). By reducing the number of charges, very heavy, highly-charged analyte ions can be converted into ions that are less highly charged, in order to reduce the complexity of the mass spectra from mixtures of large numbers of heavy analyte ions with high numbers of charges each. In the limiting case, the analyte ions or the fragment ions can be converted down to singly charged ions, which then yield mass spectra that are much easier to interpret. In some types of mass spectrometer it is only this charge reduction that makes it possible to resolve the isotope groups of all the ions signals into individual mass-to-charge ratios m/z, in order, as those skilled in the art know, to determine the number of charges z on the ions of this isotope group from the spacing between the ion signals, and so determine their physical mass m.

Under favorable conditions, the electron attachment ion source can be used to generate both types of anion—the radical anions for electron transfer dissociation and the non-radical anions for charge reduction. To a large extent this ion source is identical to conventional ion sources for negative chemical ionization (NCI), but is operated with a special gas with which the injected electrons are quickly thermalized. Methane is frequently used as the thermalization gas. Hydrogen radicals are also created by the electron bombardment. As disclosed in patent application DE 10 2006 049 241 A1, given a suitable substance, changing the voltage used to extract the anions is sufficient to deliver one type of anion or the other.

The reactions both for electron transfer dissociation and for charge reduction predominantly take place in reaction cells in which both positive and negative ions can be stored. Reactions in ion guide systems are also known. The reaction cells are often filled with a damping gas in which the ion movements are thermalized. The reaction cells may, for instance, consist of two-dimensional RF ion traps with special pseudopotential barriers at the ends, or three-dimensional RF ion traps. Devices with both kinds of reaction cell are available on the market, and are known to those skilled in the art. The positive analyte ions and the negative reactant ions are usually introduced one after the other into the ion trap where they are mixed together. The reactions then proceed without any further intervention.

In some cases, however, the fragmentation may be incomplete because the fragment ions formed by electron transfer dissociation remain associated. It is, however, also known that in such cases the associated fragment ions can be made to collide with the damping gas through gentle excitation of their secular oscillations, causing the associations to dissolve.

Quadrupole RF ion traps can be used as mass analyzers for the product ions created. It is then necessary to ensure that the form of the electrodes is very precisely hyperbolic in order to permit precisely resonant excitation, especially for the ions to be ejected with good mass resolution for their measurement. Measurement of the mass-sequentially ejected ions results in a mass spectrum. The accurate shape of the electrodes is necessary so that, by means of a harmonic pseudopotential field, the excitation frequencies of the oscillating ions are kept constant and independent of the oscillation amplitude during resonant excitation. The electrodes must therefore be shaped so that a well-formed quadrupole field is generated inside.

In some quadrupole mass spectrometers, a small proportion of higher-order multipole fields is deliberately superimposed onto the quadrupole field. Such deliberately generated deviations from a pure quadrupole field can, on the one hand, introduce non-linear, very strong and sharply defined resonance conditions and, on the other hand, hold the ions in resonance when a mass scan is in progress.

In three-dimensional ion traps, the ions mix of their own accord as they are introduced. In two-dimensional ion traps, a somewhat different procedure is sometimes used. If reactions between positive and negative ions are to be created in such linear ion traps, the clouds of positive analyte ions and the negative reactant ions are first collected in different sections, known as the prefilter and postfilter; then a special switching of the axis potentials sends them to be mixed in the central region of the linear ion trap. This method is disclosed in great detail in the patent application already cited above, US 2005/0199804 A1 (D. F. Hunt et al.).

The RF ion traps always have a low mass boundary for the storage of ions. Ions below a threshold mass m/z cannot be stored. The threshold mass is proportional to the amplitude of the RF field, and can be changed by altering the RF voltage. This phenomenon prevents light fragment ions from being stored after they have been created by the fragmentation reaction. On the other hand, the phenomenon can be exploited for ETD so that, after sufficient reaction time, excess reactant ions are very quickly ejected, in fractions of a millisecond, by briefly increasing the RF voltage, if the reactant ions are light enough. This method is more advantageous than ejection by means of resonant excitation, since the latter method takes longer because an entire isotope group always has to be ejected, and this makes a hole in the mass spectrum.

The multiply charged positive analyte ions are usually created in electrospray ion sources. This automatically generates ions that have, as a rule of thumb, approximately one charge for every 700 daltons of analyte molecule mass, although the number of charges shows a wide distribution. For analyte molecules with a physical mass of around 10,000 daltons, ions with a wide range of charge levels are created, extending from about seven to about 20 charges. For these ion mixtures, it is expedient to carry out PTR charge reduction—by means of reactions with suitable negative, non-radical reactant ions—before, during or after the electron transfer dissociation. It is therefore favorable if the non-radical reactant ions required for this can be created in the same electron attachment ion source, preferably from the same substance.

SUMMARY

In accordance with the principles of the invention, substances previously unknown for use as ETD substances are used to produce radical anions that lead to dissociations by electron transfer with a high yield of fragment ions. In addition these substances have favorable properties for their handling and for the associated analytical methods. For example, a high volatility of the substances allows them to be kept in unheated containers outside the vacuum system, making it easier to replace empty substance containers. A low molecular weight of the substances allows the measurement of even very light fragment ions, down to individual terminal amino acids. Further, such substances have the ability to also supply, by choice, non-radical anions from the electron attachment ion source for reducing the charges on the biopolymer ions or their fragment ions.

In one embodiment, substances are chosen from a class of aliphatic compounds with electron affinities between 0.3 and 0.8 electronvolts for the generation of radical anions for ETD. Few substances with known electron affinities that satisfy these conditions are found in large databases like the NIST chemistry webbook. However, through substitutions with electron-attracting or electron-repelling groups, it is often possible to first create aliphatic compounds that initially do not satisfy these conditions and then convert the aliphatic compounds into substances with suitable electron affinities and with a stability that allows radical anions to be formed that are effective for ETD. Such aliphatic hydrocarbons, or their substitutes, usually have far higher vapor pressures than the polycyclic aromatics.

Unsubstituted 1-3-5-7-cyclooctatetraene ([8]-annulene; $C_8H_8$; FIG. 1) is presented here as an example of a particularly favorable starting substance from a suitable class of aliphatic compounds. This monocyclic polyene is classified as non-aromatic and is therefore, by definition, aliphatic. In addition to a high yield of ETD fragment ions, it offers the further advantages of a moderately high vapor pressure of around 1000 pascal at 20° C., and a relatively low molecular weight of 104 daltons. 1-3-5-7-cyclooctatetraene is a chemically stable, golden-yellow liquid with a melting point of 0° Celsius and a boiling point of around 140° Celsius. The substance can be held in containers that are outside the vacuum system of mass spectrometers, at room temperature. If the thermalization gas for the electron attachment ion source, methane for instance, flows through the gas region of this container over the surface of the liquid, it transports enough substance vapor to the electron attachment ion source, where sufficient radical ions for electron transfer dissociation can be formed from this vapor. The low molecular weight of 104 daltons is advantageous in that, after mass-unstable ejection of the unused reactant ions, fragment ions of low mass can also be seen in the reaction cell, consisting of two, or even of only one amino acid. For instance, the formerly terminal $C_1$ fragment ions of 13 of the 20 amino acids can be detected.

On the other hand, non-radical anions with a mass of 99 daltons for use in charge reduction can be generated from 1-3-5-7-cyclooctatetraene in a suitable electron attachment ion source.

DETAILED DESCRIPTION

Figure 1:
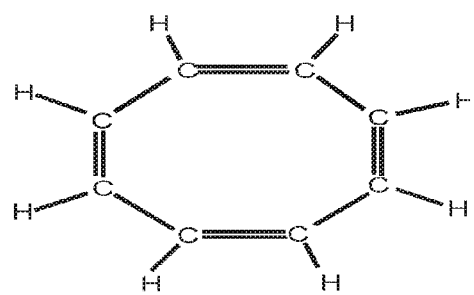
FIG. 1 illustrates the structure of 1-3-5-7-cyclooctatetraene ([8]-annulene).

While the invention has been shown and described with reference to a number of embodiments thereof, it will be recognized by those skilled in the art that various changes in form and detail may be made herein without departing from the spirit and scope of the invention as defined by the appended claims.

The invention provides aliphatic compounds with electron affinities between 0.3 and 0.8 electronvolt to generate the radical ions for electron transfer dissociation.

Electron affinity is the energy required to remove the electron from the radical anion—in other words, the binding energy of the additional electron. On the one hand, this binding energy must not be too small because the substance would scarcely pick up electrons, and, after picking up an electron, the anions would also easily lose the electron again. On the other hand, the binding energy must not be too large, as otherwise the positive biopolymer ions will not be able to attract the electron, causing detachment—in other words, electron transfer could not occur.

The term "aliphatic" is defined in organic chemistry as "non-aromatic". In the very extensive NIST database for organic substances (webbook.nist.gov), however, the table of substances with known electron affinities in the range of EA=0.3 to 0.8 eV, which has well over 200 entries (including, however, many substance anions or radicals), contains only a few such aliphatic compounds, whereas nearly all the polycyclic aromatics from the patent publication US 2005/0199804 A1 (D. F. Hunt et al.) cited above can be found there. If aliphatic compounds without metallic heteroatoms and with molecular weights between 80 and 200 daltons are considered, then only the following six substances are to be found in this range:

trichloroethene (m=131.39 Da; EA=0.400 eV);
1,1,1,3,3,3-hexafluoro-2-propanone (m=166.02 Da; EA=0.442 eV);
tetrafluorofuran-2,5-dione (perfluoro-succinic acid anhydride, m=172.03 Da; EA=0.500 eV);
1,3,5,7-cyclooctatetraene (m=104.15 Da; EA=0.550 eV);
tetrachloroethene (m=165.83 Da; EA=0.64 eV);
2,3-butanedione (m=86.09 Da; EA=0.69 eV).

Since it is occasionally advantageous to use very heavy radical anions, the $C_{84}$ fullerene, which has a molecular weight of m=1008.9 Da and an electron affinity of EA=0.41 eV, should also be mentioned here.

Not all of these substances, however, supply suitable radical anions for electron transfer dissociation. For example, after picking up an electron in the electron attachment ion source, tetrafluorofuran-2,5-dione decomposes into a more stable ion that is no longer suitable for donating electrons.

Fundamental considerations suggest that substances with double bonds, particularly polyenes, are especially advantageous substances. Polyenes are organic compounds containing two or more carbon-carbon double bonds. Depending on the number of carbon-carbon double bonds in the molecule, the polyenes are classified as dienes (with two double bonds), trienes (with three), tetraenes (with four), pentaenes (with five) etc.

Monocyclic polyenes, which according to Hückel's rule have only 4n π-electrons in the ring instead of the 4n+2 π-electrons of the aromatics (where n=0, 1, 2, 3 . . . ), belong to the so-called "anti-aromatics". They are not aromatic compounds, as is also shown by NMR analysis, and are therefore classified as aliphatic. According to the HMO model of Hückel, anti-aromatics have unfavorable energy levels. They are therefore less stable than aromatic compounds.

To supplement the substances listed in the NIST table, it is possible to produce additional aliphatic compounds by substituting appropriate groups to change the electron affinity of aliphatic hydrocarbons. In order to change the electron affinity by means of appropriate substituents, heteroatoms such as nitrogen, oxygen or sulfur can be substituted for carbon atoms, or chemical groups can be inserted instead of the hydrogen atoms. Electron-attracting groups, such as the cyano group (which yields nitriles), the nitro group or the halogens such as fluorine, chlorine or bromine, increase the electron affinity. Electron-repelling groups, on the other hand, such as nitrites or ether groups (yielding O-alkyls) lower the electron affinity.

As an example here we consider isoamyl nitrite ($C_5H_{11}NO_2$), which is produced as an aliphatic ester of nitrous acid with a molecular weight of m=117.15 Da. Its use as a substance for ETD, however, showed that an anion with a mass of m=85 Da formed as a decomposition product in the electron attachment ion source. Although this anion was able to create electron transfer dissociation, the effectiveness was not in the desired range.

As an exceptionally successful example from the aliphatic polyene substance class, we should mention unsubstituted 1-3-5-7-cyclooctatetraene (COT), which also has other favorable properties in addition to a high yield of fragment ions when used for ETD. Cyclooctatetraene with four double bonds in a ring of eight (see FIG. 1) is a golden yellow liquid with a vapor pressure around 1000 pascal at 20° Celsius. It is no more poisonous than many other chemicals used in the laboratories concerned, and is therefore easy to handle. Cyclooctatetraene possesses 8 π-electrons, and therefore belongs to the anti-aromatics. It is non-planar, so the double bonds are not conjugated (as NMR investigations also show); for this reason too, it is not classified as aromatic, and is therefore aliphatic. The electron affinity is 0.55 eV. It yields radical anions with a mass of 104 daltons, and these provide an outstanding yield of fragment ions when used for electron transfer dissociation. All the hydrogen atoms are "vinylic" and therefore very strongly bonded to the carbon atom, which simply means that the radical anion of COT is quite stable.

Figure 3:
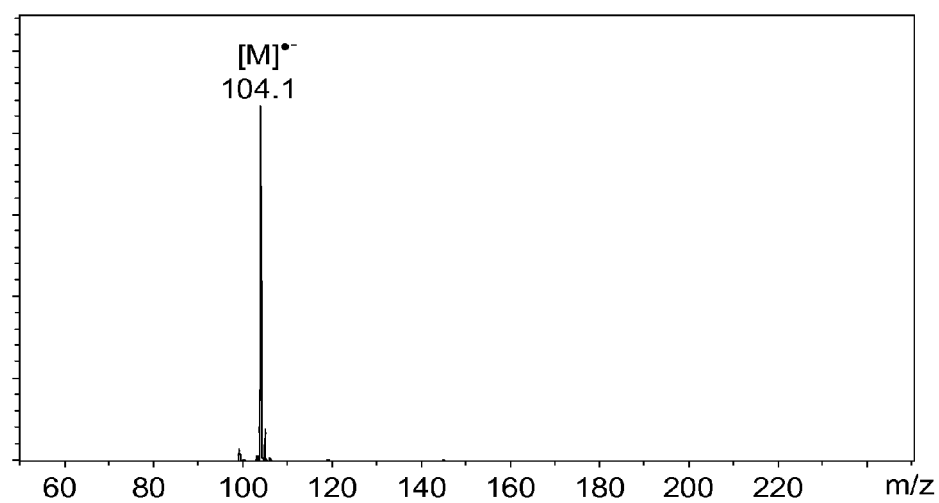
FIG. 3 shows a spectrum of negative ions produced from cyclooctatetraene with the radical anion at a mass of 104 Da, which greatly predominates here and is used to carry out the electron transfer dissociation. Next to it, a weak signal can also be seen at a mass of 99 Da, formed by a non-radical anion. It can be preferentially extracted by switching over the electron attachment source, and so used for charge reduction.
Figure 4:
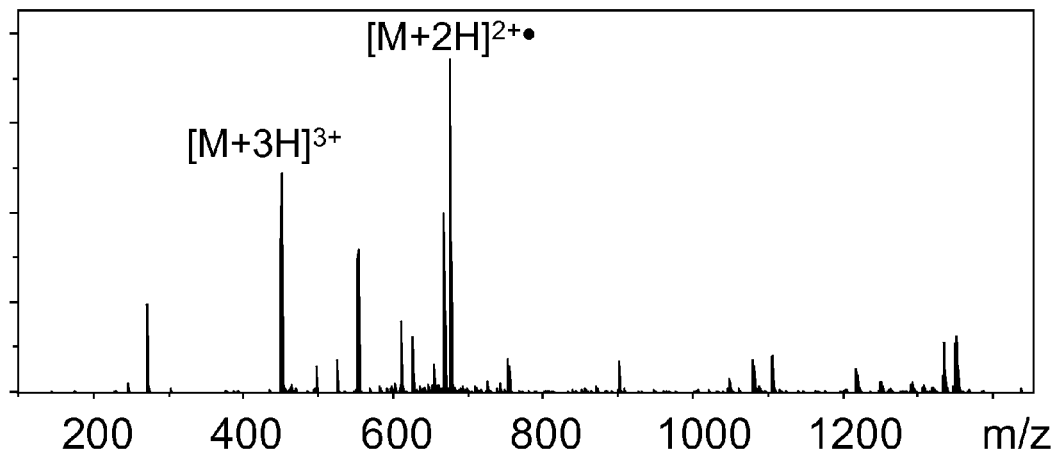
FIG. 4 shows a mass spectrum of the positively charged fragment ions that are created by ETD with cyclooctatetraene radical anions from triply charged ions of the peptide "substance P" (molecular weight 1347.66 Da).
Figure 5:
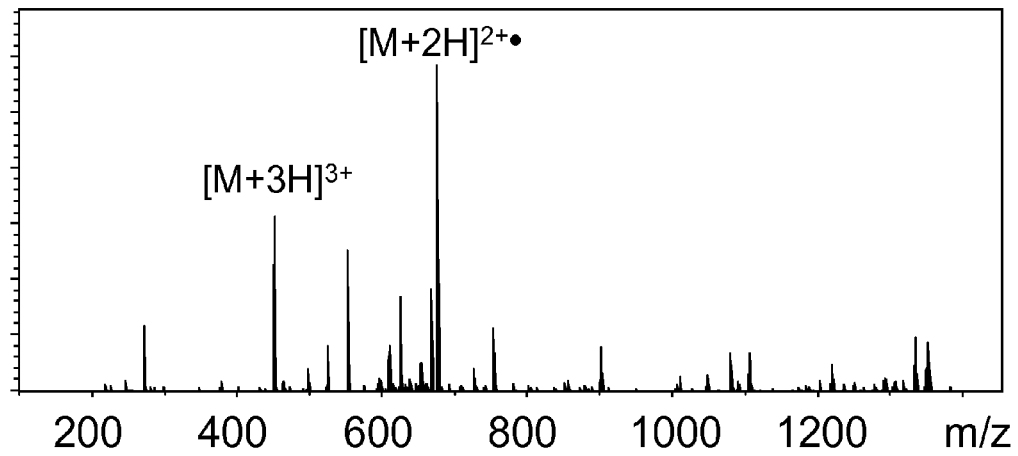
FIG. 5 shows, for comparison, a conventional mass spectrum of the fragment ions from triply charged ions of substance P, generated with radical anions of fluoranthene. The comparison shows that the effectiveness of the two starting substances is of a similar magnitude. The same fragment ions are formed. The slight variations in intensities are normal for spectra that are obtained from a single filling of the reaction cell.

FIGS. 3 and 4 show the mass spectra of the radical anions of 1-3-5-7-cyclooctatetraene and the dissociation products from substance P obtained using it. For comparison, FIG. 5 shows the dissociation products of substance P obtained with radical anions of fluoroanthene. It can be seen that the ETD-effectiveness of the radical ions of the two starting substances is similar, and that exactly the same fragment ion species are formed. The slight differences in intensities are within the normal range of variations for single spectra.

Some forms of 1-3-5-7-cyclooctatetraene obtained through alkyl substitution (alkyl=methyl, ethyl, propyl, isobutyl), and some forms of cyclooctatetraene with heteroatoms are also suitable for the creation of ETD reactant ions.

We should mention that the patent application cited above, US 2005/0199804 A1 (D. F. Hunt et al.), also reports investigations of the use of anions of non-aromatic substances for ETD. For example, perfluorotributylamine, sulfur hexafluoride and perfluoro-1,3-dimethylcyclohexane were examined. As expected, the anions of these substances generated electron transfer dissociation, but only to a very small extent, while simultaneously occurring proton transfer reactions were dominant, meaning that these substances do not have high ETD efficiency. These investigations therefore have little to do with the invention described here, instead, they point in precisely the opposite direction, as is shown by the focus of the further work carried out on polycyclic aromatics by the working group around D. F. Hunt.

Figure 2:
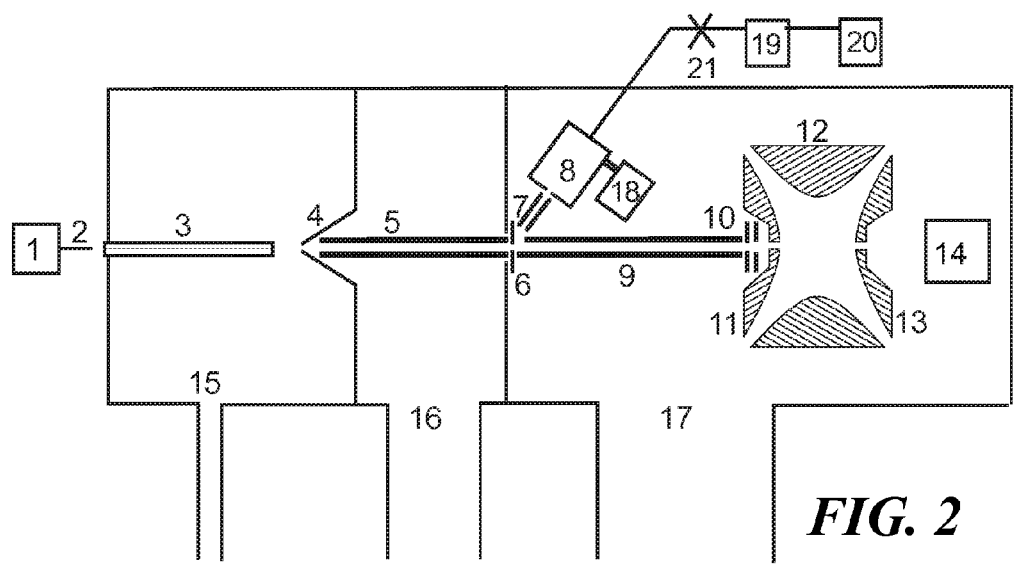
FIG. 2 is a diagram of an ion trap mass spectrometer in which ETD can be carried out, with an electrospray ion source (1, 2) to generate multiply charged positive analyte ions, an electron attachment ion source (8) to generate the negatively charged reactant ions (radical anions), and the end cap electrodes (11, 13) and ring electrode (12) of a 3D ion trap that serves as the reaction cell for the ETD. The ion guide (9), here implemented as a multipole rod system, can feed both positive and negative ions to the ion trap. According to the prior art, the substance used to produce the radical anions is kept in a heated container (18) close to the ion source (8); the use of volatile starting substances in accordance with this invention makes it possible, however, to mount a substance container (19), through which methane gas flows from a reservoir (20), outside the vacuum system and without heating.

A favorable embodiment of an ion trap mass spectrometer suitable for carrying out a method according to the invention is shown schematically in FIG. 2. Here, an electrospray ion source (1) with a spray capillary (2) is used outside the mass spectrometer's vacuum system to ionize biopolymers. It will be assumed here that a mixture of digestion peptides from a large protein is to be analyzed. The ions are fed in the usual way through an inlet capillary (3) and a skimmer (4) with the ion guide systems (5) and (9), through the pressure stages (15), (16), (17), into a 3D ion trap with end cap electrodes (11 and 13) and a ring electrode (12), where they are trapped in the usual way. The ion guide systems (5) and (9) consist of parallel pairs of rods to which alternating phases of a RF voltage are applied. They can be implemented as quadrupole, hexapole or octopole rod systems.

A first mass spectrum, acquired by resonant excitation of the ions with mass-selective ejection and measurement of the ejected ions in the ion detector (14), provides an overview of the digestion peptides, since almost exclusively ionized molecules rather than fragment ions, albeit with various levels of charge, are formed in the electrospray ion source. If one or more peptides are now to be analyzed to find their sequence of amino acids, then usual techniques are applied to isolate, for example, the triply charged ions of this peptide; this means that the ion trap is first overfilled, and then all the ions that are not triply charged ions of this peptide are ejected from the ion trap. The triple charge can be recognized from the spacing of the isotopic lines which for triply charged ions is precisely ⅓ of an atomic mass unit. If not enough triply charged ions are available, it is also possible to use ions with a different level of charge.

The oscillations of these now isolated, multiply charged ions are then damped and the ions are assembled in the center of the trap during a brief pause of a few milliseconds by the action of the collision gas, which is always present. Then the negatively charged reaction ions are added. These ions are generated here in a separate ion source (8) for negative chemical ionization (an electron attachment ion source), and channeled through a small ion guide (7) to an ion switch, where they are threaded into the ion guide system (9) leading to the ion trap (11, 12, 13). Ion guide systems of this kind can convey both positive and negative ions. In the embodiment illustrated, the ion switch consists simply of an apertured diaphragm (6), to which suitable DC potentials can be applied, and a shortening of one or two of the rods that comprise the ion guide (9). It is particularly advantageous for this very simple type of ion switch to use an octopole system as the ion guide and to just shorten two pole rods. If suitable voltages are applied to the apertured diaphragm (6), this ion switch can allow the ions from the electrospray ion source (1, 2) to pass unhindered; with other voltages the negative ions from the ion source (8) are reflected into the ion guide (9). They pass via this ion guide (9) into the ion trap, where they are held in the usual way by an injection lens (10). They react immediately (within a few milliseconds) with the positive ions.

According to the prior art, the low vapor pressure of the substances used to produce the radical ions meant that these substances had to be kept in a container (18) that could be heated to between 50° and 250° Celsius, and was mounted close to the electron attachment ion source (8), which was also heated. In most cases, no valves were used, so it was not possible to shut off the substance container. As described above in the introductory section, this arrangement is disadvantageous because it causes the substances to be consumed rapidly, and refilling with substance requires the mass spectrometer's vacuum system to be vented. The invention allows substances with high vapor pressure to be used for ETD, which means that the substance, for instance the cyclooctatetraene, can be held in a container (19) outside the mass spectrometer's vacuum system. This makes refilling very easy.

The container (19) can, moreover, be kept at room temperature, thus avoiding the difficulty of having to feed a heated gas line through the unheated walls of the vacuum system. For example, methane used as a thermalization gas for the electron attachment ion source can flow directly from a reservoir (20) through this container (19). The methane transports enough substance to create the radical anions. A valve (21) can easily be installed to allow the gas line to be closed so that the supply of substance and thermalization gas can be interrupted if necessary. It is also possible to use several substances alternately by means of several containers and several valves.

In the process of electron transfer dissociation, the fragment ions that are formed sometimes remain associated and form radical cations which, although not very stable, do not immediately decay. It is therefore advantageous to apply a weak, dipolar, AC excitation voltage to the two end caps (11, 13) of the ion trap to generate resonant excitation of these radical cations. The frequency required for this AC excitation voltage can be calculated from the known mass of these radical cations and from their known charge. The effect of this excitation voltage is that these radical cations quickly decay, for which only relatively weak impacts are needed, and the yield of the desired fragment ion species is thereby increased.

The non-radical anions with a mass of m=99 Da that are generated from the cyclooctatetraene in the electron attachment ion source can successfully be used for charge reduction by proton transfer reactions. Unfortunately, initial trials did not achieve an entirely clean extraction of the radical anions from the ion source. However, since charge reduction and electron transfer dissociation are usually carried out simultaneously in order to save time, the ion species that have not been cleanly separated can nevertheless be used effectively. The ratio of the two types of ion can be adjusted between broad limits by means of the extraction voltage at the ion source.

It is probable that the conditions for extracting the non-radical ions from the ion source can be improved through design modifications. However, if, in accordance with the invention, the substance container is mounted at ambient temperature outside the vacuum system with a valve in the gas line, it is also easily possible to introduce other substances with similar vapor pressures from additional containers and through additional valves into the electron attachment ion source; one of these substances can, for instance, be used solely for creating non-radical anions if a clean proton transfer reaction without simultaneous ETD is required.

Given the knowledge that substances with low vapor pressure or low molecular weight can also be used as substances for the production of radical anions for ETD, those skilled in the art can take further measures that make it easier to handle the mass spectrometer or to carry out analytical procedures.

What is claimed is:

1. A mass spectrometer having a vacuum system and comprising:
    an electron attachment ion source that is located inside the vacuum system and produces radical anions for electron transfer dissociation of biopolymers from a substance;
    a container for the substance that is located outside the vacuum system; and
    a transport system for transporting the substance from the container to the electron attachment ion source.

2. The mass spectrometer of claim 1, wherein the container is maintained at ambient temperature.

3. The mass spectrometer of claim 1, wherein the transport system also transports to the electron attachment ion source a thermalization gas that carries a vapor of the substance from the container to the electron attachment ion source.

4. The mass spectrometer of claim 1, further comprising a valve in the transport system located between the container and the electron attachment ion source for controlling the flow of the substance to the electron attachment ion source.

5. The mass spectrometer of claim 4, further comprising a plurality of containers, each container containing a substance for producing radical anions for electron transfer dissociation of biopolymers and being attached to the transport system by a valve to control the flow of the contained substance to the electron attachment ion source.

6. The mass spectrometer of claim 5, wherein the electron attachment ion source is constructed to generate non-radical ions for charge reduction by proton transfer reactions in addition to radical anions for electron transfer dissociation of biopolymers.

7. The mass spectrometer of claim 5, wherein one of the plurality of containers contains a substance for the generation of non-radical ions for charge reduction.

8. The mass spectrometer of claim 1, wherein the electron attachment ion source is constructed to generate non-radical ions for charge reduction by proton transfer reactions in addition to radical anions for electron transfer dissociation of biopolymers.

9. The mass spectrometer of claim 8, wherein the electron attachment ion source is constructed to generate the non-radical anions and the radical anions from the same substance.

* * * * *